United States Patent [19]

Fugoso

[11] Patent Number: 5,497,782
[45] Date of Patent: Mar. 12, 1996

[54] LOCKABLE GUIDEWIRE

[75] Inventor: Mauricio L. Fugoso, Chula Vista, Calif.

[73] Assignee: Medtronic, Inc., Minneapolis, Minn.

[21] Appl. No.: 235,115

[22] Filed: Apr. 28, 1994

[51] Int. Cl.⁶ .................................................. A61M 25/01
[52] U.S. Cl. .............................................. 128/772; 604/95
[58] Field of Search ............................ 604/95; 128/772

[56] References Cited

U.S. PATENT DOCUMENTS

| | | | |
|---|---|---|---|
| 4,430,083 | 2/1984 | Ganz et al. | 128/772 |
| 5,002,560 | 3/1991 | Machold et al. | 604/95 |
| 5,273,052 | 12/1993 | Kraus et al. | 128/772 |
| 5,275,173 | 1/1994 | Samson et al. | 128/772 |
| 5,282,478 | 2/1994 | Fleischhaker, Jr. et al. | 128/772 |
| 5,339,833 | 8/1994 | Berthiaume et al. | 128/772 |
| 5,372,144 | 12/1994 | Mortier et al. | 128/772 |
| 5,373,856 | 12/1994 | Grenouillet | 128/772 |
| 5,379,779 | 1/1995 | Rowland et al. | 128/772 |

FOREIGN PATENT DOCUMENTS

| | | |
|---|---|---|
| 0416734 | 8/1989 | European Pat. Off. . |
| 0415332 | 8/1989 | European Pat. Off. . |

*Primary Examiner*—Paul J. Hirsch
*Attorney, Agent, or Firm*—Michael R. Shevlin; Dianne M. F. Plunkett; Harold R. Patton

[57] ABSTRACT

A system for inserting and exchanging a dilatation catheter (18) using a lockable guidewire (23) and a guide catheter (17). The locking mechanism is engaged when a hypotube (31) is retracted in the locking section (8) and exposes the radially expanding corewire (30) which locks the guidewire (23) in place in the guiding catheter (17). The guiding catheter (17) may have a modified catheter inner surface (13) lined with a means for frictional engagement with the radially expanding corewire (30). In one embodiment the guiding catheter (17) can be lined with a threaded means complementary to radially expanding corewire (30) helical coil for mechanically holding the lockable guidewire (23) in place. Once locked, the guidewire (23) remains fixed in relation to the lesion (20) during the exchange of a dilatation catheter (18).

22 Claims, 3 Drawing Sheets

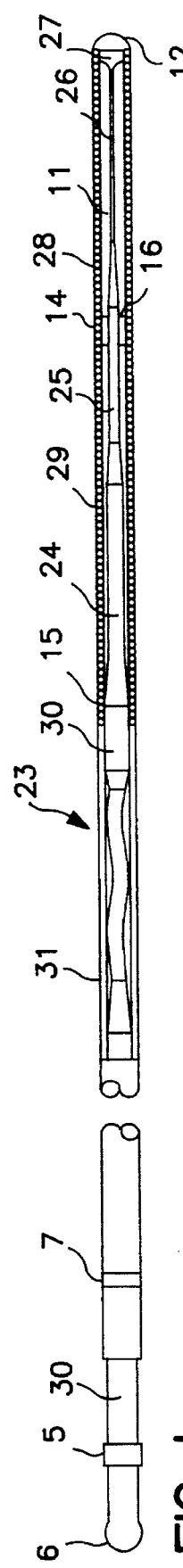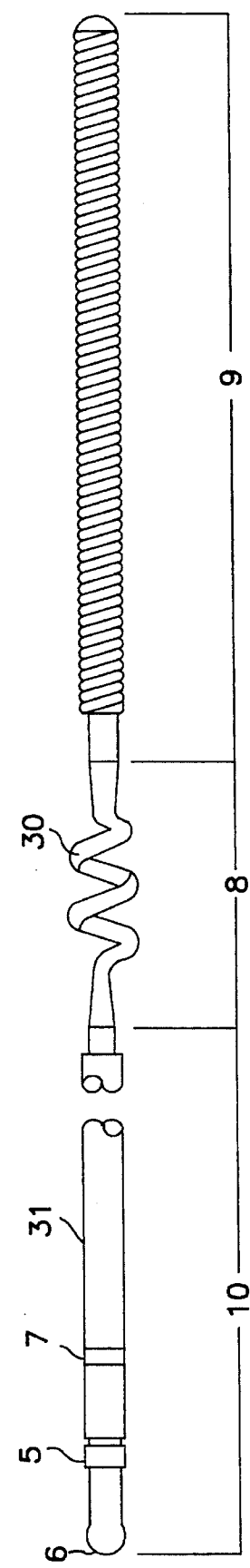
FIG. 1
FIG. 2

LOCKABLE GUIDEWIRE

FIELD OF THE INVENTION

The present invention relates to field of angioplasty, and more particularly, to an apparatus and method of locking a disposable guidewire to facilitate the exchange of a balloon catheter.

BACKGROUND OF THE INVENTION

Dilatation balloon catheters are frequently used for the treatment of stenosis in the coronary arteries. This procedure, known as percutaneous transluminal coronary angioplasty (PCTA), was developed by Dr. Andreas Gruntzig. According to this procedure, blockage in a coronary artery can be reduced by positioning a balloon dilatation catheter across the blockage and inflating the balloon, which causes the blockage to decrease. The first marketable PCTA catheters for angioplasty were "fixed wire" catheters, in which a core or guidewire was fixed within the catheter to stiffen it so that it could be pushed into position in the vascular system.

Dr. John Simpson and Dr. Edward Robert subsequently developed an "over-the-wire" catheter in which a guidewire was slidably placed within a lumen of the catheter. The guidewire lumen passed from the distal end of the catheter through the balloon to the proximal end of the catheter. This system provided reasonably easy placement of the catheter because the guidewire was inherently smaller and more flexible than the fixed wire system so one could more readily select the desired coronary artery and reach smaller branches. Once the guidewire was positioned beyond the stenosis, the catheter was then slid over the guidewire so that placement of the balloon spanned the stenosis and the balloon was then inflated. When performing a PCTA, a physician will commonly use a series of balloon dilatation catheters. Each of the catheters has a different shape, size or configuration suited for a particular purpose. The old "fixed wire" catheter acts as its own guidewire, so that the exchange of catheters requires removal of the entire assembly from the stenosis area and the path back to the stenosis must be re-established each time. This is time consuming and difficult for the physician. The "over the wire" catheter uses a separate guidewire that can be left in place during the exchange and used as the path for the insertion of the new catheter. One of the problems with the "over the wire" exchange is the inability to maintain position of the guidewire within the vascular system during the exchange.

It is desirable to maintain position of the guidewire during the exchange of catheters to ensure safety and speed of the angioplasty procedure. To do this, the guidewire must be held in place during the exchange. Approaches to this problem have included use of long or exchangeable guidewires or extendable guidewires. During a catheter exchange, the proximal portion of the guidewire that extends outside of the body is held so the guidewire position across the stenosis is maintained. The length of guidewire used during the exchange that extends outside the body must be longer than the length of the dilatation balloon catheter to provide a means to hold the guidewire at all times to prevent inadvertent withdrawal of the guidewire as the catheter is withdrawn. However, guidewire movement relative to the stenosis still occurs despite such external fixation of the guidewire. One of the reasons for this is that the length of wire external to the body is approximately 150 cm long (either using a extension wire or a 300 cm long guidewire). This length of wire is often cumbersome and difficult to handle while maintaining the guidewire position across the stenosis.

Rapid exchange catheters have been developed with shorter guidewire lumens passing from the distal end of the catheter through the balloon and opening to the exterior of the catheter somewhere proximal to the balloon; they make the catheter exchange over the guidewire easier to accomplish. One of the problems presented with these is that because the guidewire only extends through a relatively small portion of the overall length of the catheter, the remaining portion of the catheter shaft is unsupported by the guidewire. The unsupported portion tends to buckle within the guide catheter, increasing the contact area between the catheter shaft and inner surface of the guide catheter thus increasing friction and causing the balloon catheter to bind up.

Recently, other schemes have been developed for catheter exchange using balloons to trap the guidewire, shown in European Patent Application Publication number 0416734A1 to Coehlo and European Patent Application Publication number 0415332A1 to Keith. Both of the above use balloons that are either part of the guide catheter or separate from both the guidewire and guide catheter and are then inflated to trap the guidewire in place during the exchange. While both of these may work, they use up precious space needed by the catheter.

SUMMARY OF THE INVENTION

The present invention allows a standard length guidewire to be used for a catheter exchange. In using the lockable guidewire of the present invention, a dilatation catheter exchange can be accomplished using one standard length guidewire without an extension guidewire. The locking mechanism is engaged when a hypotube sleeve is retracted and exposes the radially expanding corewire that locks the guidewire in place in the guiding catheter. The radially expanding corewire may be shaped in many forms such as sinusoidal, helical coil or zigzag. The guiding catheter can be lined with a threaded means complementary to the radially expanding corewire for mechanically holding the guidewire in place or the guiding catheter can be lined with a material providing a frictional engagement with the radially expanding corewire. Once locked in place, the guidewire will keep its position in relation to the stenosis and allow the exchange of the catheter.

BRIEF DESCRIPTION OF THE DRAWINGS

FIG. 1 is a perspective and section view of the guidewire according to the present invention configured as a guidewire with locking section 8 covered by a hypotube 31;

FIG. 2 is a perspective view of the guidewire configured as a locking guidewire with locking section 8 uncovered by a hypotube 31;

DETAILED DESCRIPTION OF THE PREFERRED EMBODIMENTS

Figure 3:
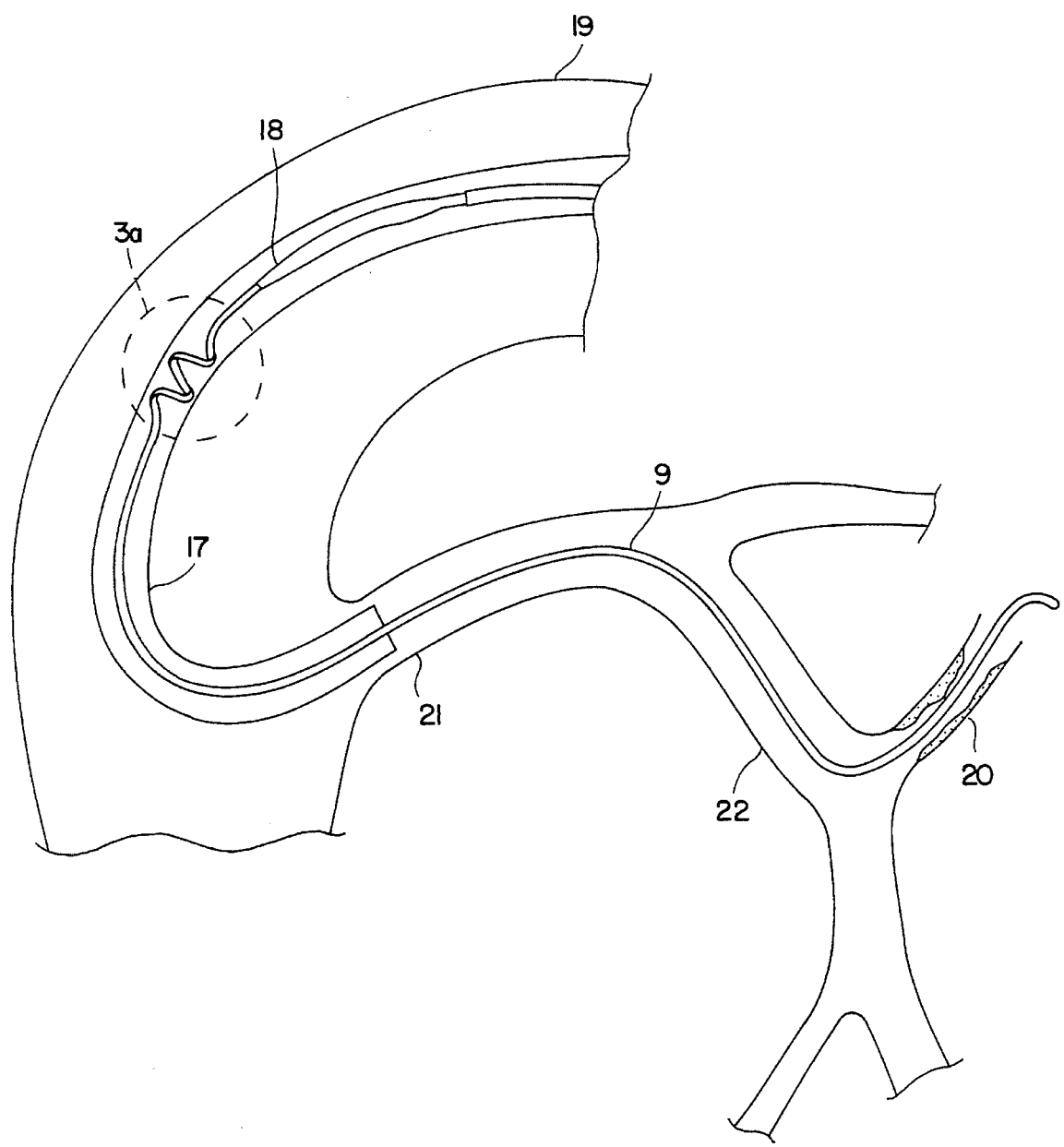
FIG. 3 is a view of the guidewire in the locking configuration inside a guiding catheter during exchange of a dilatation catheter.

The lockable guidewire in FIG. 1 shows the complete assembly of the invention in the unlocked configuration with locking section 8 covered by hypotube 31. FIG. 2 shows the guidewire in the locked configuration with locking section 8 uncovered exposing the radially expanding corewire 30. The lockable guidewire is comprised of three sections: the locking section 8, the floppy section 9 which is at the distal end, and the stiff section 10. Along the entire length of the lockable guidewire is a unitary torque-transmitting corewire 30 that is made from a 0.229 mm diameter (0.009") stainless steel wire, work hardened by drawing, or of a shape memory wire such as nickel titanium. The corewire 30 diameter varies along the three sections. Along the stiff section 10, the diameter of corewire 30 is 0.229 mm (0.009") with a length of approximately 152 cm. Along the locking section 8, the diameter of corewire 30 is 0.127 mm (0.005") or more with a length of 2.5 cm. Along the floppy section 9, with a length of approximately 30 cm, corewire 30 consists of a combination of three step-down diameters of 0.203 mm (0.008") 24, 0.152 mm (0.006") 25 and 0.076 mm (0.003") 26 and a distal end step-up diameter 27 of 0.229 mm (0.009") with a length of 0.1 cm at the distal end. The smallest step down diameter 26 (0.076 mm) is then flattened to form flattened section 11 with a cross section of 0.025 mm (0.001")×0.152 mm (0.006"), with an approximate length of 1 cm.

The distal end of a platinum coil spring 28, with an outer diameter of 0.356 mm (0.014") and a inner diameter of 0.254 mm (0.010") and a length of 3 cm, is welded to distal end step up diameter 27 of corewire 30 and forms a ball tip 12. The proximal end of the platinum coil spring 28 is then concentrically brazed 14 to a spring brace 16. The distal end of a stainless steel spring coil 29, with a outer diameter of 0.356 mm (0.014") and a inner diameter of 0.254 mm (0.010") and a length of 26 cm, is concentrically brazed 14 to the proximal end of the platinum coil spring 28 and the spring brace 16. The proximal end of stainless steel spring coil 29 is then concentrically brazed 15 to corewire 30.

The locking section 8 is formed from corewire 30 by radially expanding the corewire to form an outside diameter which is approximately 10–30% greater than the inside diameter of the guiding catheter. The radial expansion of the corewire can be many shapes such as sinusoidal, zigzag or a helical coil as shown in FIG. 2. The radially expanded corewire 30 should be large enough to contact the modified catheter inner surface 13 to lock as shown in FIG. 3a. In the unlocked configuration a hypotube 31, with a marker 7 near the proximal end, is slid over the radially expanded corewire 30 to the proximal end of the stainless steel spring coil 29 to cover the locking section 8. To slide the hypotube 31 over the locking section 8, one has to pull corewire 30 and longitudinally extend the locking section 8 so as to reduce the expanded diameter of corewire 30 to fit inside the hypotube 31 as shown in FIG. 1. A stopper ring 5 is brazed to the proximal end of corewire 30 and stops the hypotube 31 from coming off when it is proximally slid to fully open the locking section 8 as shown in FIG. 2. The proximal end of corewire 30 is then welded to form a ball tip shape 6.

The locking guidewire 23 fits inside a guiding catheter 17 and can be locked in place. The guiding catheter 17 may have a modified catheter inner surface 13 as shown in FIG. 3a. The modified catheter inner surface 13 is lined with a means for frictional engagement of the radially expanded corewire 30 when the locking section 8 is open for mechanically holding the locking guidewire 23 in place. FIG. 3a shows one configuration where the modified catheter inner surface 13 means for frictional engagement is a threaded means complementary to a helical coil expanded corewire 30 for frictional engagement. Once the expanded corewire 30 engages the modified catheter inner surface 13, the locking guidewire 23 remains fixed during the exchange of the dilatation catheter 18.

Figure 3A:
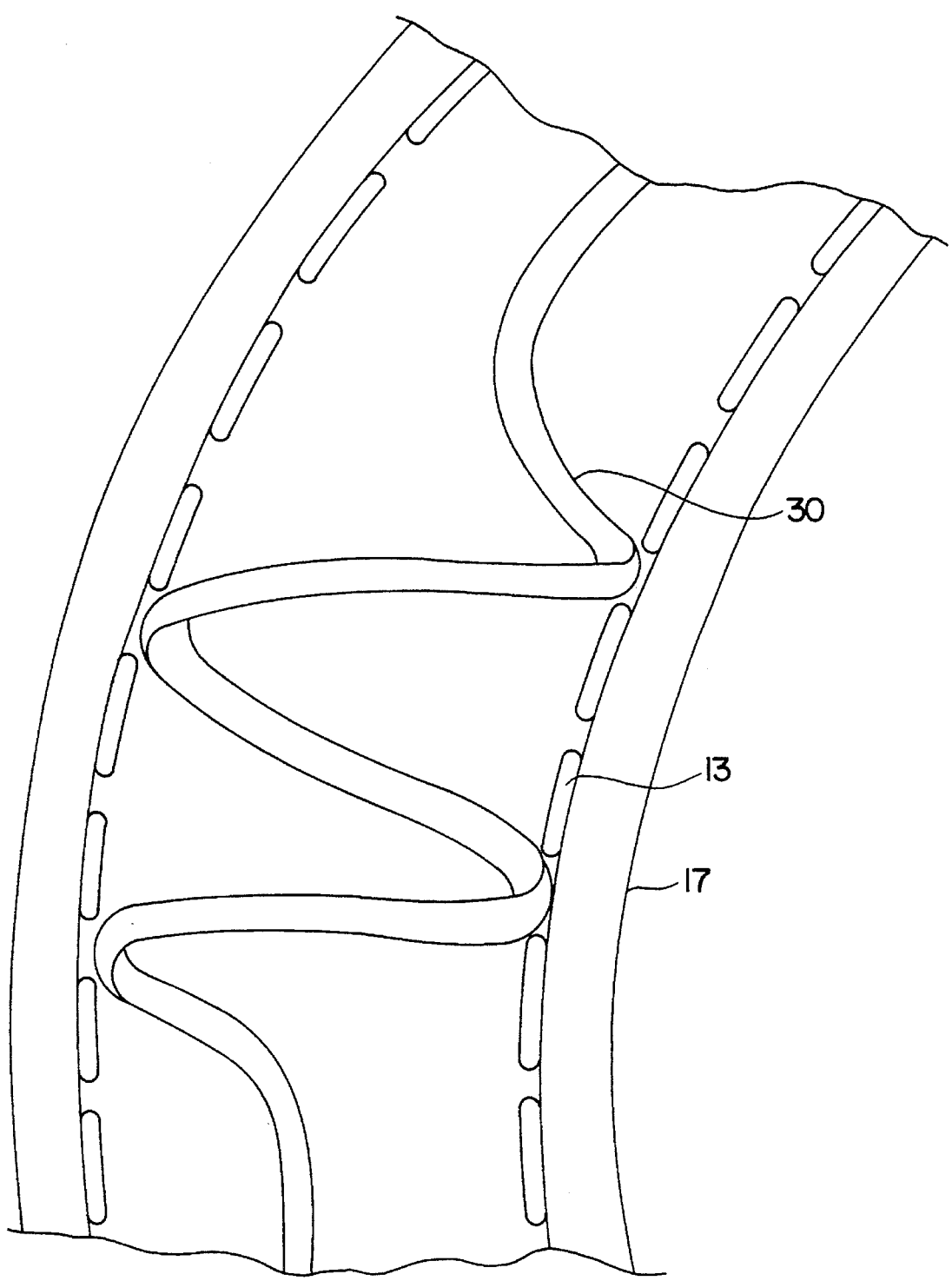
FIG. 3a is an exploded view of the guidewire locked in place inside a modified guiding catheter.

The method of using the invention is as follows:

At the beginning of a PTCA procedure, the guiding catheter 17 with the modified catheter inner surface 13 is inserted into the body, through the aorta 19 with the distal end in the ostium 21, as shown in FIG. 3. Once the guiding catheter 17 is in place, the lockable guidewire is inserted through the guiding catheter 17 the until its distal end has crossed the lesion 20 in the artery 22. After the lockable guidewire 23 is in the correct place, it can be locked for the insertion of an over the wire dilatation catheter 18.

To lock the lockable guidewire 23 in place in the guiding catheter 17 while leaving the guidewire across the lesion, secure the corewire 30 at the proximal end between the ball tip shape 6 and the stopper ring 5 and uncover the locking section 8 by pulling the hypotube 31 until it contacts the stopper ring 5, releasing the radially expanding corewire 30 to engage the modified catheter inner surface 13. The lockable guidewire 23 is now locked inside the guiding catheter 17 as shown in FIGS. 3 & 3a.

The dilatation catheter 18 can now be inserted. Insert the dilatation catheter over the lockable guidewire 23 until the proximal end of the dilatation catheter 18 is aligned to marker 7. Secure the corewire 30 at the proximal end between the ball tip shape 6 and the stopper ring 5 and slide hypotube 31 forward until it stops against the stainless spring coil 29 and covers the radially expanded corewire 30 of locking section 8. Secure the lockable guidewire 23 and advance the dilatation catheter 18 to the lesion 20.

Sometimes the dilatation catheter 18 must be exchanged. This is common when a different balloon diameter is required for the lesion 20. The preferred method of keeping the guidewire across the lesion 20 during the catheter exchange is as follows. The lockable guidewire 23 is secured and the dilatation catheter 18 is pulled back until the proximal end of the dilatation catheter 18 is aligned with marker 7. Next, secure the corewire 30 at the proximal end between the ball tip shape 6 and the stopper ring 5 and uncover the locking section 8 by pulling the hypotube 31 until it contacts the stopper ring 5, releasing the radially expanding corewire 30 to engage the modified catheter inner surface 13. The lockable guidewire 23 is now locked inside the guiding catheter 17 and the dilatation catheter 18 can be removed. Finally, insert a new dilatation catheter 18 as before.

The preceding specific embodiments are illustrative of the practice of the invention. It is to be understood, however, that other expedients known to those skilled in the art or disclosed herein, may be employed without departing from the spirit of the invention or the scope of the appended claims.

| No. | Component |
| --- | --- |
| 5 | Stopper ring |
| 6 | Ball Tip Shape |
| 7 | Marker |
| 8 | Locking Section |
| 9 | Floppy Section |
| 10 | Stiff Section |
| 11 | Flattened Section |
| 12 | Ball Tip |
| 13 | Modified Catheter Inner Surface |
| 14 | Braze |
| 15 | Braze |
| 16 | Spring Brace |
| 17 | Guiding Catheter |
| 18 | Dilatation Catheter |
| 19 | Aorta |
| 20 | Lesion |

-continued

| No. | Component |
|---|---|
| 21 | Ostium |
| 22 | Artery |
| 23 | Locking Guidewire |
| 24 | Step-down Diameter |
| 25 | Step-down Diameter |
| 26 | Step-down Diameter |
| 27 | Step-up Diameter |
| 28 | Platinum coil spring |
| 29 | Stainless spring coil |
| 30 | Corewire |
| 31 | Hypotube |

What is claimed is:

1. A lockable guidewire comprising:
    (a) a proximal section with a proximal end and a distal end;
    (b) a locking section with a proximal end and a distal end;
    (c) a distal section with a proximal end and a distal end;
    (d) the distal end of the proximal section is contiguous with the proximal end of the locking section, the distal end of the locking section is contiguous with the proximal end of the distal section;
    (e) the locking section having a radially expanding means for anchoring the lockable guidewire within a guiding catheter; and
    (f) a means for retaining and releasing the radially expanding means within the locking section.

2. The lockable guidewire of claim 1 wherein the means for retaining and releasing is a hypotube which is slidable between the distal end of the locking section surrounding the radially expanding means and the proximal end of the locking section uncovering and releasing the radially expanding means.

3. A lockable guidewire according to claim 2 further comprising a marker on the hypotube to indicate when a catheter surrounding the guidewire has been withdrawn to a position proximal to the radially expanding means.

4. A catheter system comprising:
    (a) a lockable guidewire according to claim 1; and
    (b) a guiding catheter wherein the guiding catheter is lined with a means for frictional engagement with the radially expanding means for mechanically holding the lockable guidewire in place.

5. The catheter system according to claim 4 wherein the means for frictional engagement with the radially expanding means is a threaded means complementary to the radially expanding means for mechanically holding the lockable guidewire in place.

6. A method of anchoring a lockable guidewire within a guiding catheter comprising the following steps:
    (a) providing a guiding catheter with an inside surface;
    (b) providing a lockable guidewire according to claim 1;
    (c) inserting the lockable guidewire in the guiding catheter;
    (d) moving the retaining means of the lockable guidewire to release the radially expanding means that engages the inside surface of the guiding catheter for mechanically holding the lockable guidewire in place.

7. A method of anchoring a lockable guidewire within a guiding catheter comprising the following steps:
    (a) providing a catheter system according to claim 4;
    (b) inserting the lockable guidewire in the guiding catheter;
    (c) moving the retaining means of the lockable guidewire to release the radially expanding means that engages the means for frictional engagement lining the guiding catheter for mechanically holding the lockable guidewire in place.

8. A lockable guidewire used in conjunction with a guiding catheter to facilitate the exchange of a balloon catheter comprising:
    (a) a proximal section with a proximal end and a distal end;
    (b) a locking section with a proximal end and a distal end;
    (c) a distal section with a proximal end and a distal end;
    (d) the distal end of the proximal section is contiguous with the proximal end of the locking section, the distal end of the locking section is contiguous with the proximal end of the distal section;
    (e) the locking section having a radially expanding means for anchoring the lockable guidewire within a guiding catheter such that the guidewire position is maintained relative to the guiding catheter; and
    (f) a means for retaining and releasing the radially expanding means within the locking section.

9. The lockable guidewire according to claim 8 wherein the means for retaining and releasing is a hypotube which is slidable between the distal end of the locking section surrounding the radially expanding means and the proximal end of the locking section uncovering and releasing the radially expanding means.

10. A lockable guidewire according to claim 9 further comprising a marker on the hypotube to indicate when a catheter surrounding the guidewire has been withdrawn to a position proximal to the radially expanding means.

11. A catheter system comprising:
    (a) a lockable guidewire according to claim 8; and
    (b) a guiding catheter wherein the guiding catheter is lined with a means for frictional engagement with the radially expanding means for mechanically holding the lockable guidewire in place.

12. The catheter system according to claim 11 wherein the means for frictional engagement with the radially expanding means is a threaded means complementary to the radially expanding means for mechanically holding the lockable guidewire in place.

13. A method of anchoring a lockable guidewire within a guiding catheter comprising the following steps:
    (a) providing a guiding catheter with an inside surface;
    (b) providing a lockable guidewire according to claim 8;
    (c) inserting the lockable guidewire in the guiding catheter;
    (d) moving the retaining means of the lockable guidewire to release the radially expanding means that engages the inside surface of the guiding catheter for mechanically holding the lockable guidewire in place.

14. A method of anchoring a lockable guidewire within a guiding catheter comprising the following steps:
    (a) providing a catheter system according to claim 11;
    (b) inserting the lockable guidewire in the guiding catheter;
    (c) moving the retaining means of the lockable guidewire to release the radially expanding means that engages the means for frictional engagement lining the guiding catheter for mechanically holding the lockable guidewire in place.

15. A lockable guidewire comprising:

(a) a proximal section with a proximal end and a distal end;

(b) a locking section with a proximal end and a distal end;

(c) a distal section with a proximal end and a distal end;

(d) the distal end of the proximal section is contiguous with the proximal end of the locking section, the distal end of the locking section is contiguous with the proximal end of the distal section;

(e) the locking section having a radially expanding means for anchoring the lockable guidewire within a guiding catheter; and (f) a hypotube which is slidable between the distal end of the locking section surrounding the radially expanding means and the proximal end of the locking section uncovering and releasing the radially expanding means.

16. A lockable guidewire according to claim 15 further comprising a marker on the hypotube to indicate when a catheter surrounding the guidewire has been withdrawn to a position proximal to the radially expanding means.

17. A catheter system comprising:

(a) a lockable guidewire according to claim 15; and (b) a guiding catheter wherein the guiding catheter is lined with a means for frictional engagement with the radially expanding means for mechanically holding the lockable guidewire in place.

18. The catheter system according to claim 17 wherein the means for frictional engagement with the radially expanding means is a threaded means complementary to the radially expanding means for mechanically holding the lockable guidewire in place.

19. A catheter system comprising:

(a) a lockable guidewire according to claim 15; and (b) a guiding catheter wherein the guiding catheter is lined with a threaded means complementary to the radially expanding means for mechanically holding the lockable guidewire in place.

20. A method of anchoring a lockable guidewire within a guiding catheter comprising the following steps:

(a) providing a guiding catheter with an inside surface;

(b) providing a lockable guidewire according to claim 15;

(c) inserting the lockable guidewire in the guiding catheter;

(d) moving the hypotube of the lockable guidewire to release the radially expanding means that engages the inside surface of the guiding catheter for mechanically holding the lockable guidewire in place.

21. A method of anchoring a lockable guidewire within a guiding catheter comprising the following steps:

(a) providing a catheter system according to claim 17;

(b) inserting the lockable guidewire in the guiding catheter;

(c) moving the retaining means of the lockable guidewire to release the radially expanding means that engages the means for frictional engagement lining the guiding catheter for mechanically holding the lockable guidewire in place.

22. A method of anchoring a lockable guidewire within a guiding catheter comprising the following steps:

(a) providing a catheter system according to claim 19;

(b) inserting the lockable guidewire in the guiding catheter;

(c) moving the hypotube of the lockable guidewire to release the radially expanding means that engages the threaded means lining the guiding catheter for mechanically holding the lockable guidewire in place.

* * * * *